US010603031B2

(12) United States Patent
Sauer

(10) Patent No.: US 10,603,031 B2
(45) Date of Patent: Mar. 31, 2020

(54) SUTURING DEVICE FOR MINIMALLY INVASIVE SURGERY

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 153 days.

(21) Appl. No.: 15/889,107

(22) Filed: Feb. 5, 2018

(65) Prior Publication Data

US 2018/0221012 A1   Aug. 9, 2018

Related U.S. Application Data

(60) Provisional application No. 62/454,708, filed on Feb. 3, 2017.

(51) Int. Cl.
*A61B 17/04* (2006.01)
*A61B 17/062* (2006.01)
*A61B 17/00* (2006.01)
*A61B 17/06* (2006.01)

(52) U.S. Cl.
CPC ...... *A61B 17/0469* (2013.01); *A61B 17/0625* (2013.01); *A61B 2017/00367* (2013.01); *A61B 2017/00783* (2013.01); *A61B 2017/047* (2013.01); *A61B 2017/0472* (2013.01); *A61B 2017/0608* (2013.01); *A61B 2017/06042* (2013.01)

(58) Field of Classification Search
CPC ............ A61B 17/0469; A61B 17/0625; A61B 2017/00367; A61B 2017/00783; A61B 2017/047; A61B 2017/0472; A61B 2017/06042; A61B 2017/0608
See application file for complete search history.

(56) References Cited

U.S. PATENT DOCUMENTS

| 2,646,045 A | 7/1953 | Priestly |
| 5,431,666 A | 7/1995 | Sauer |
| 5,562,686 A | 10/1996 | Sauer |

(Continued)

FOREIGN PATENT DOCUMENTS

| EP | 1945107 | 7/2008 |
| EP | 1839592 | 12/2011 |

(Continued)

OTHER PUBLICATIONS

Apr. 30, 2015 International Search Report; Thomas, Shane: ISR for PCT/US2014/068742.

(Continued)

*Primary Examiner* — Jocelin C Tanner
(74) *Attorney, Agent, or Firm* — David J. Gervasi; Christopher B. Miller

(57) ABSTRACT

A suturing device for minimally invasive surgery is disclosed. The device has at least one ferrule holder. The device also has a latch spring comprising at least one latch biased to cover the at least one ferrule holder. The device further has a needle comprising one or more curved needle arms. The device also has a needle control wire coupled to the needle for moving the one or more curved needle arms on an arcuate path through a tissue gap. The device further has a cam coupled to the needle control wire for selective engagement with a follower region on the latch spring.

12 Claims, 18 Drawing Sheets

(56) References Cited

U.S. PATENT DOCUMENTS

| | | |
|---|---|---|
| 5,713,910 A | 2/1998 | Gordon |
| 5,741,279 A | 4/1998 | Gordon |
| 5,766,183 A | 6/1998 | Sauer |
| 5,860,990 A | 1/1999 | Nobles |
| 5,911,727 A | 6/1999 | Taylor |
| 6,368,334 B1 | 4/2002 | Sauer |
| 6,533,796 B1 | 3/2003 | Sauer |
| 6,997,931 B2 | 2/2006 | Sauer |
| 7,211,093 B2 | 5/2007 | Sauer |
| 7,407,505 B2 | 8/2008 | Sauer |
| 7,731,727 B2 | 6/2010 | Sauer |
| 7,862,572 B2 | 1/2011 | Meade |
| 7,993,354 B1 | 8/2011 | Brecher |
| 8,021,376 B2 | 9/2011 | Takemoto |
| 8,066,737 B2 | 11/2011 | Meade |
| 8,313,496 B2 | 11/2012 | Sauer |
| 8,398,657 B2 | 3/2013 | Sauer |
| 8,652,149 B2 | 2/2014 | Sauer |
| 8,852,212 B2 | 10/2014 | McClurg |
| 9,017,346 B2 | 4/2015 | Kia |
| 2002/0107530 A1 | 8/2002 | Sauer |
| 2004/0068272 A1 | 4/2004 | Sauer |
| 2004/0236356 A1 | 11/2004 | Rioux |
| 2005/0165419 A1 | 7/2005 | Sauer |
| 2007/0162052 A1 | 7/2007 | Hashimoto |
| 2007/0255296 A1 | 11/2007 | Sauer |
| 2009/0222027 A1 | 9/2009 | Sauer |
| 2011/0118758 A1 | 5/2011 | Sauer |
| 2011/0190793 A1 | 8/2011 | Nobles |
| 2012/0016383 A1 | 1/2012 | Sauer |
| 2012/0165838 A1 | 6/2012 | Kobylewski |
| 2013/0245646 A1 | 9/2013 | Lane |
| 2014/0214038 A1 | 7/2014 | Mordehai |
| 2014/0276989 A1 | 9/2014 | Lane |
| 2015/0057683 A1 | 2/2015 | Meade |
| 2015/0127024 A1 | 5/2015 | Berry |
| 2016/0345959 A1 | 12/2016 | Sauer |
| 2017/0360432 A1* | 12/2017 | Sauer ................ A61B 17/0469 |

FOREIGN PATENT DOCUMENTS

| | | |
|---|---|---|
| WO | WO1995011630 | 5/1995 |
| WO | WO2014052599 | 4/2014 |
| WO | WO2014164868 | 10/2014 |
| WO | WO2015085145 | 6/2015 |

OTHER PUBLICATIONS

Jan. 1, 2003 Product Literature; LSI Solutions® Sew-Right SR.5™, The Single Squeeze Suturing Devicett™.

Jan. 1, 2007 LSI Solutions® RD Technology Guide.

Oct. 3, 2009 LSI Solutions® RD Running Device™ Surgery's Best Suturing Technology™.

Jun. 16, 2010 Symposium; Knight, Peter, for Presentation at the STS 2011 Annual Meeting-Automated Remote Transapical Wound Closure System: Fresh Porcine Heart Bursting Pressure Study and Cadaver Endoscopic Demonstration.

Jun. 21, 2010 Symposium; Leigh, H. for Presentation at the STS 2011 Annual Meeting—Fresh Porcine Heart Bursting Pressure Study Fig. 1.

\* cited by examiner

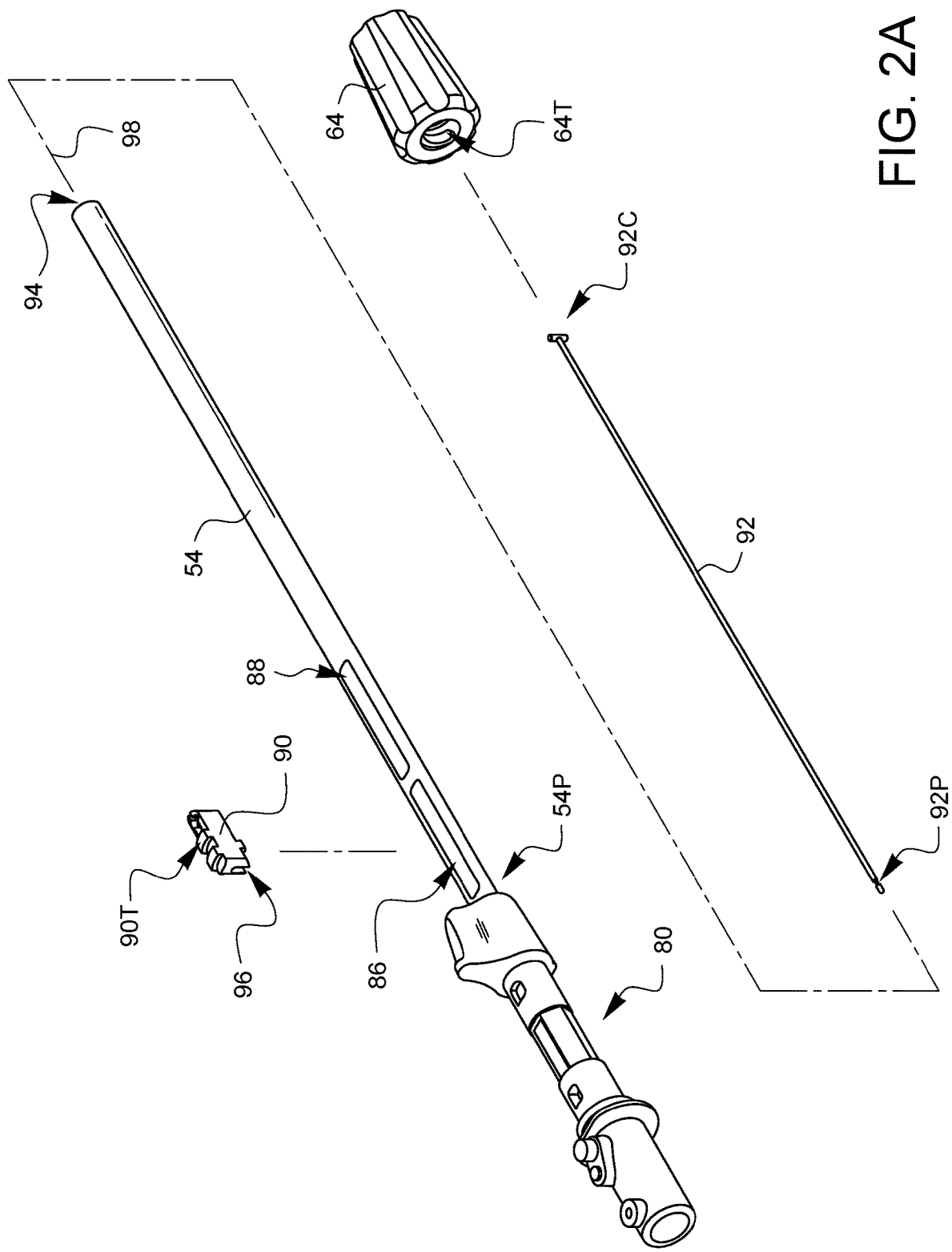

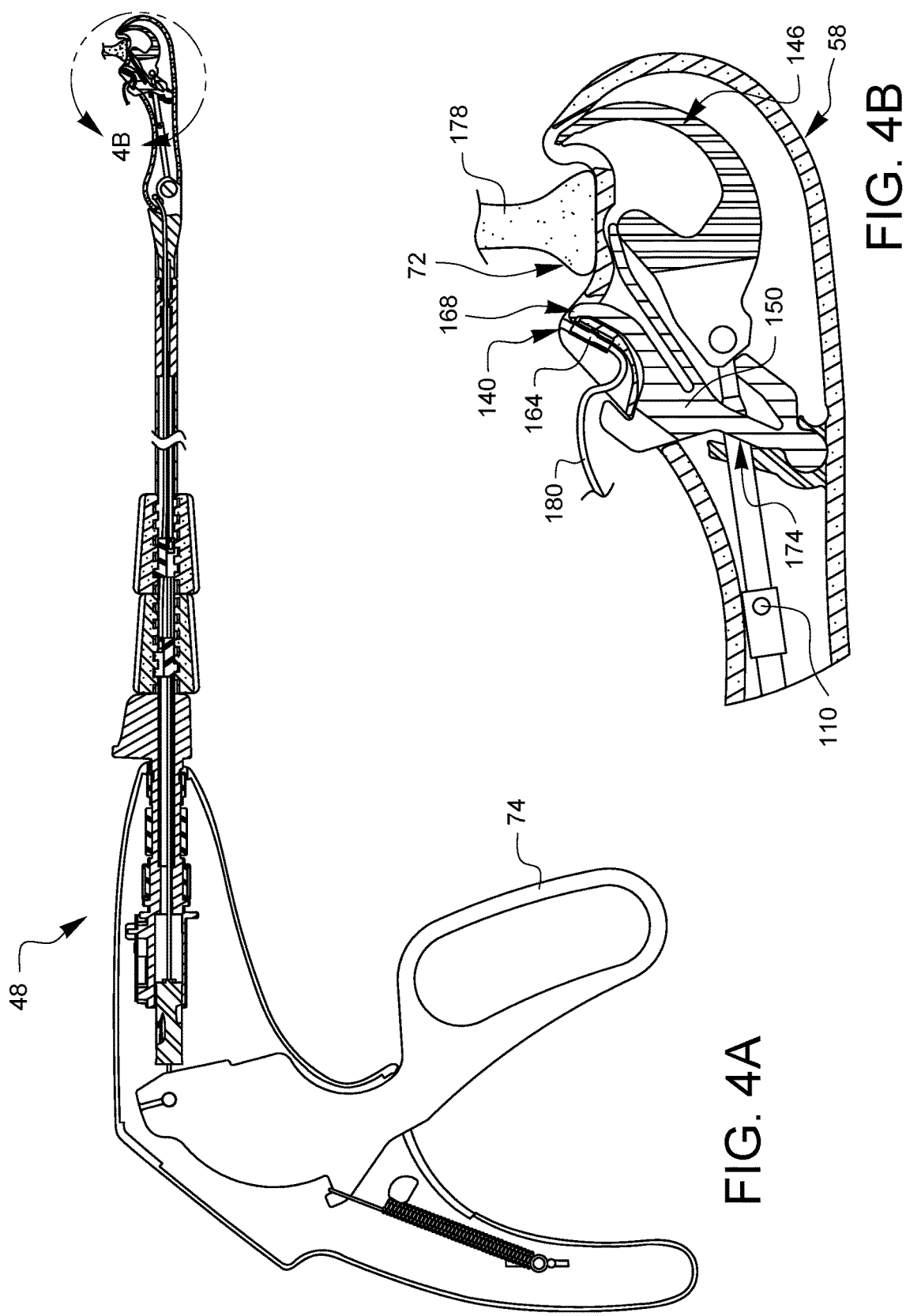

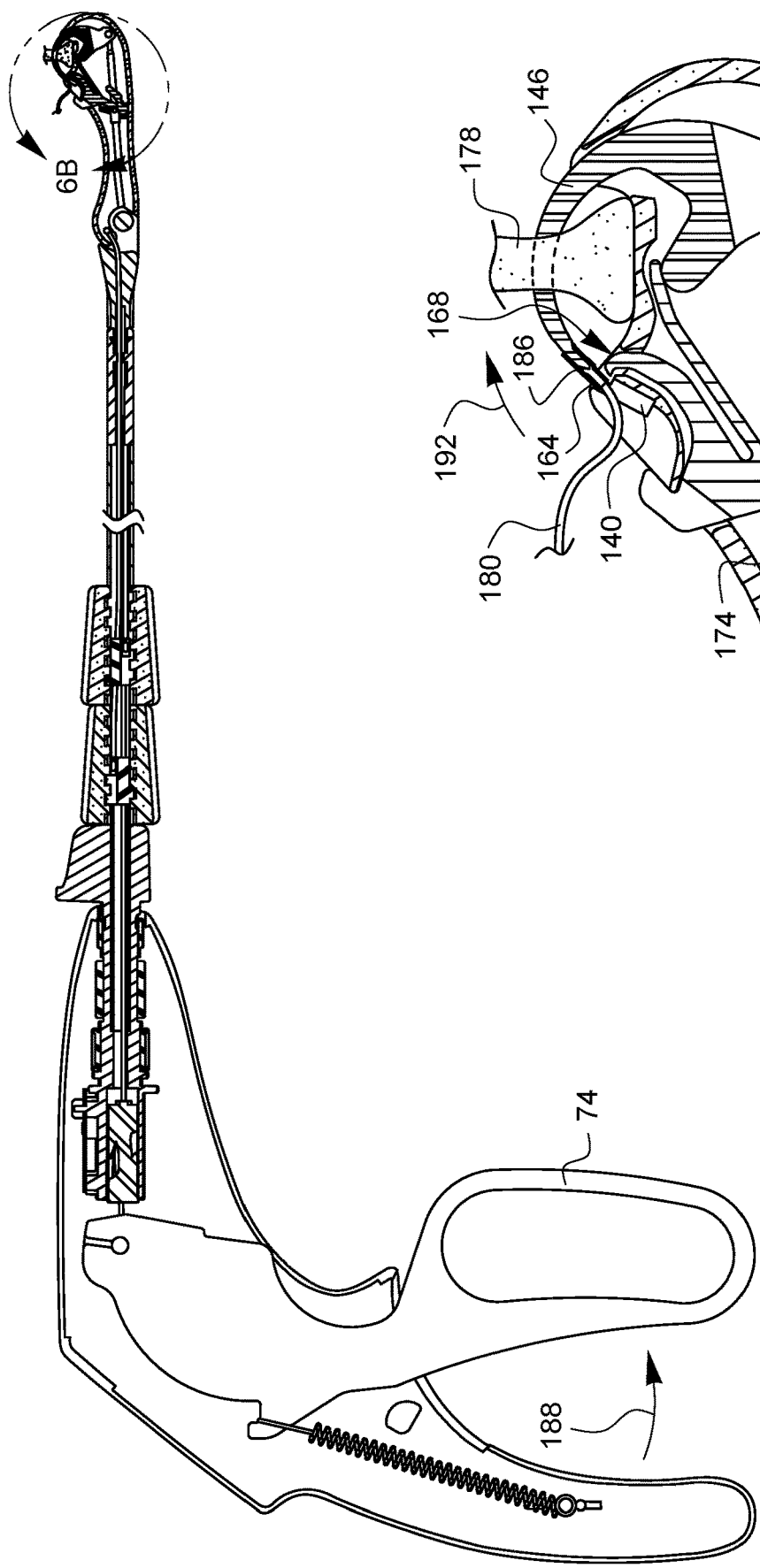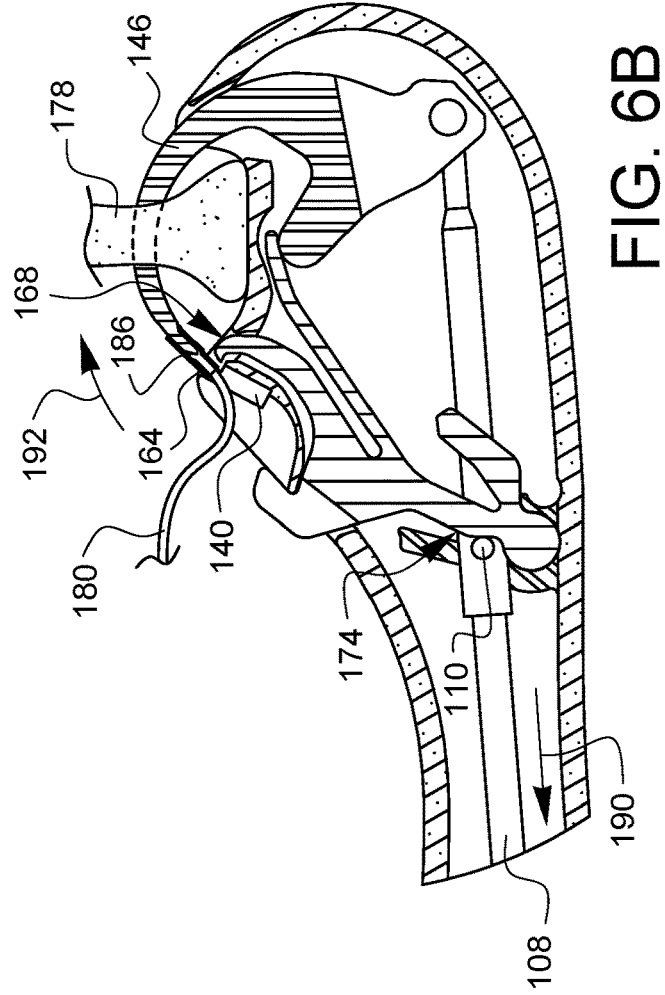

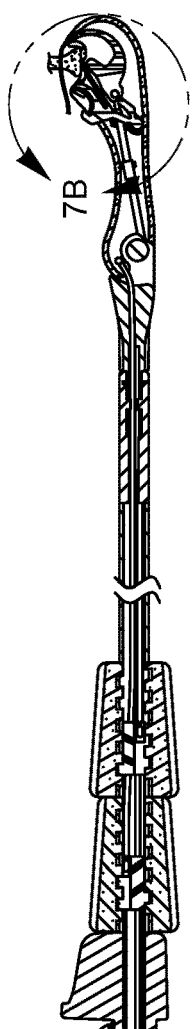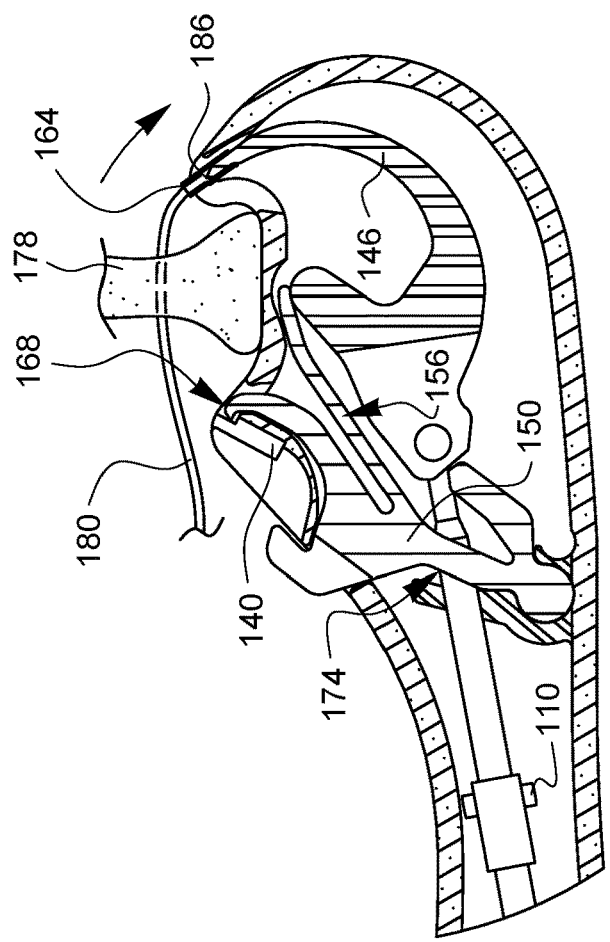
FIG. 7A
FIG. 7B

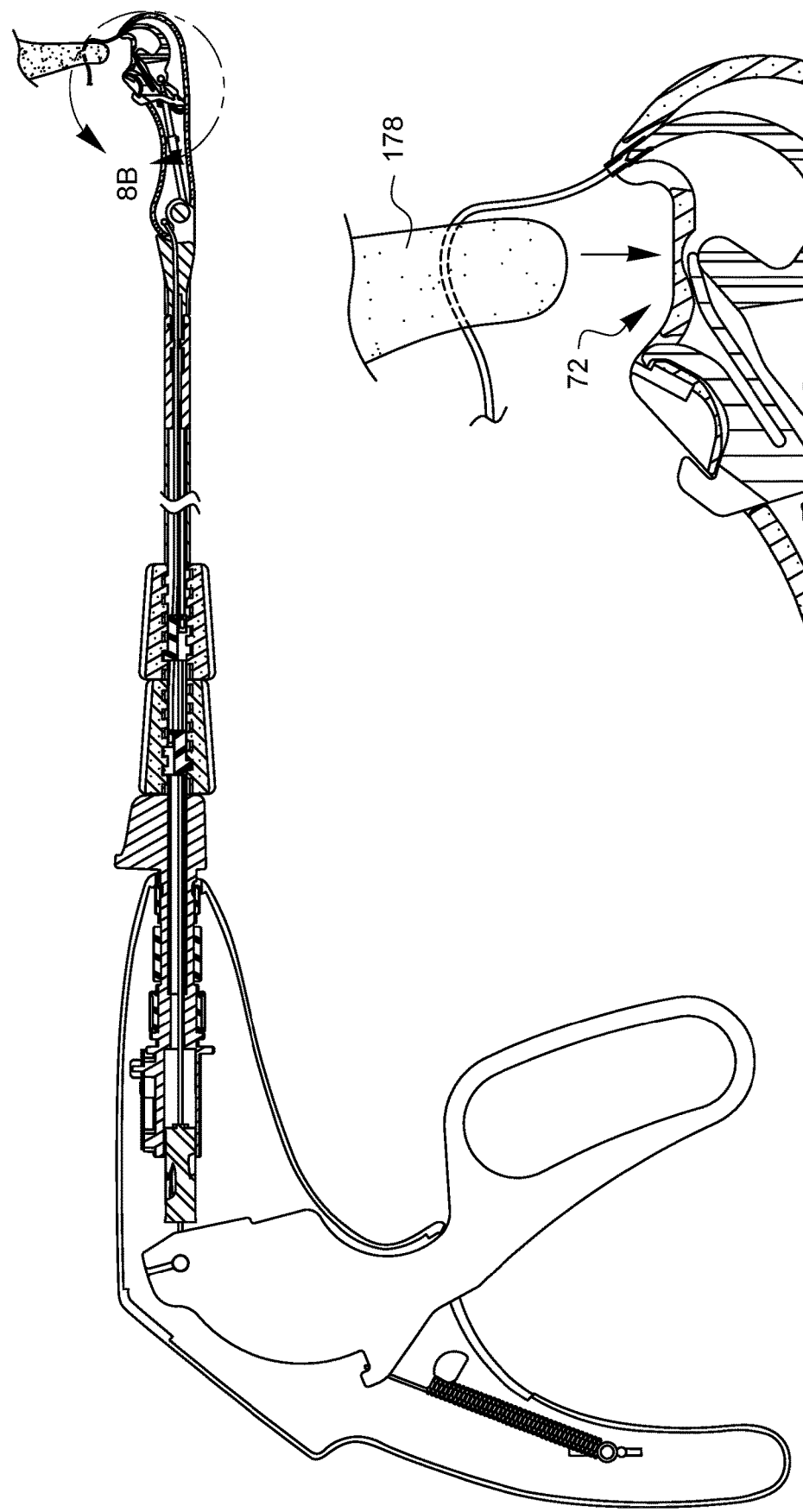

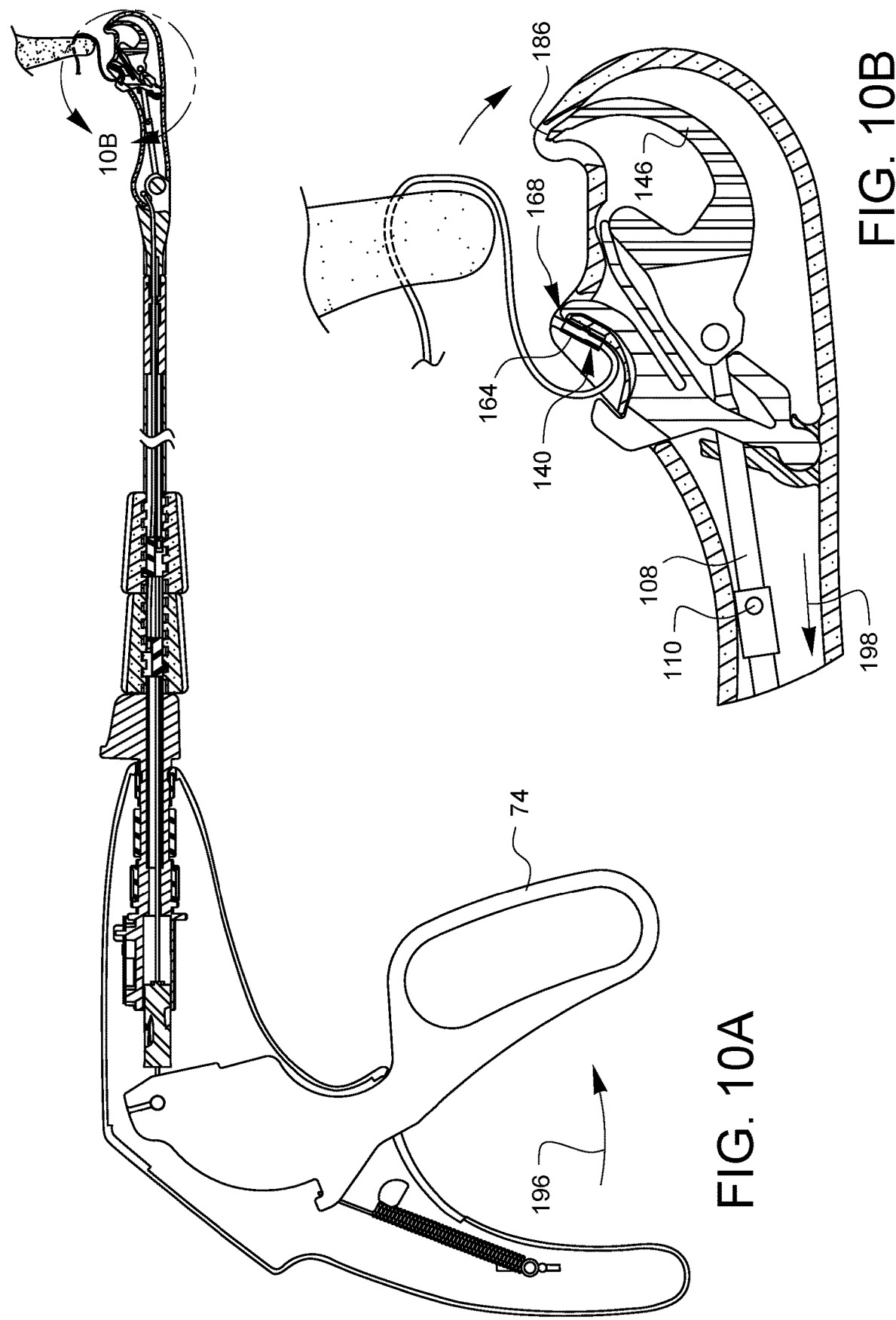

SUTURING DEVICE FOR MINIMALLY INVASIVE SURGERY

RELATED APPLICATIONS

This patent application claims priority to U.S. Provisional Patent Application No. 62/454,708 filed Feb. 3, 2017 and entitled, "SUTURING DEVICE FOR MINIMALLY INVASIVE SURGERY". The 62/454,708 application is hereby incorporated by reference in its entirety.

FIELD

The claimed invention relates to surgical suturing, and more specifically to minimally invasive surgical suturing devices.

BACKGROUND

The human heart relies on a series of one-way valves to help control the flow of blood through the chambers of the heart. Deoxygenated blood returns to the heart, via the superior vena cava and the inferior vena cava, entering the right atrium. The heart muscle tissue contracts in a rhythmic, coordinated heartbeat, first with an atrial contraction which aids blood in the right atrium to pass through the tricuspid valve and into the right ventricle. Following atrial contraction, ventricular contraction occurs and the tricuspid valve closes. Ventricular contraction is stronger than atrial contraction, assisting blood flow through the pulmonic valve, out of the heart via the pulmonary artery, and to the lungs for oxygenation. Following the ventricular contraction, the pulmonic valve closes, preventing the backwards flow of blood from the pulmonary artery into the heart.

Oxygenated blood returns to the heart, via the pulmonary veins, entering the left atrium. Left atrial contraction assists blood in the left atrium to pass through the mitral valve and into the left ventricle. Following the atrial contraction, ensuing ventricular contraction causes mitral valve closure, and pushes oxygenated blood from the left ventricle through the aortic valve and into the aorta where it then circulates throughout the body. Under nominal conditions, prolapse of the mitral valve is prevented during ventricular contraction by chordae attached between the mitral valve leaflets and papillary muscles located in the left ventricle. Following left ventricular contraction, the aortic valve closes, preventing the backwards flow of blood from the aorta into the heart.

Unfortunately, one or more of a person's heart valves can have or develop problems which adversely affect the valves' function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve fails to properly close during a ventricular contraction. Mitral regurgitation can be caused by chordae stretching, tearing, or rupturing, along with other structural changes within the heart.

Neochordal replacement for stretched or torn chordae is one option to reduce regurgitation. In such a procedure, chords to be replaced are identified and dissected as required. A papillary suture is placed in a papillary muscle corresponding to the dissected chord. The papillary suture may optionally be pledgeted on one or both sides of the papillary muscle. A leaflet suture is also placed in the corresponding mitral valve leaflet. The papillary suture and the leaflet suture may then be tied or otherwise fastened together to create a replacement chord to help support the mitral valve leaflet and prevent regurgitation.

Unfortunately, while the above techniques are proven methods of heart valve repair, technical challenges impede their widespread utilization, especially in minimally invasive cardiac surgery. While minimally invasive surgery can dramatically reduce patient recovery times by avoiding the need for full or partial sternotomy, it is difficult and time consuming to manipulate a suture needle with forceps through a minimally invasive opening between adjacent ribs to place the sutures for neochordal replacement. An innovative system that remotely delivers and reliably places suture for minimally invasive neochordal replacement would be highly desirable.

SUMMARY

A suturing device for minimally invasive surgery is disclosed. The device has at least one ferrule holder. The device also has a latch spring comprising at least one latch biased to cover the at least one ferrule holder. The device further has a needle comprising one or more curved needle arms. The device also has a needle control wire coupled to the needle for moving the one or more curved needle arms on an arcuate path through a tissue gap. The device further has a cam coupled to the needle control wire for selective engagement with a follower region on the latch spring

BRIEF DESCRIPTION OF THE DRAWINGS

FIGS. 2A-2F are exploded views illustrating assembly of the minimally invasive surgical suturing device of FIG. 1A.

FIGS. 4A, 5A, 6A, 7A, 8A, 9A, and 10A are partial cross-sectional side views illustrating a suturing sequence using the minimally invasive surgical suturing device of FIG. 1A.

FIGS. 4B, 5B, 6B, 7B, 8B, 9B, and 10B are enlarged views of FIGS. 4A, 5A, 6A, 7A, 8A, 9A, and 10A, respectively, showing the distal tip in more detail.

Figure 1A:
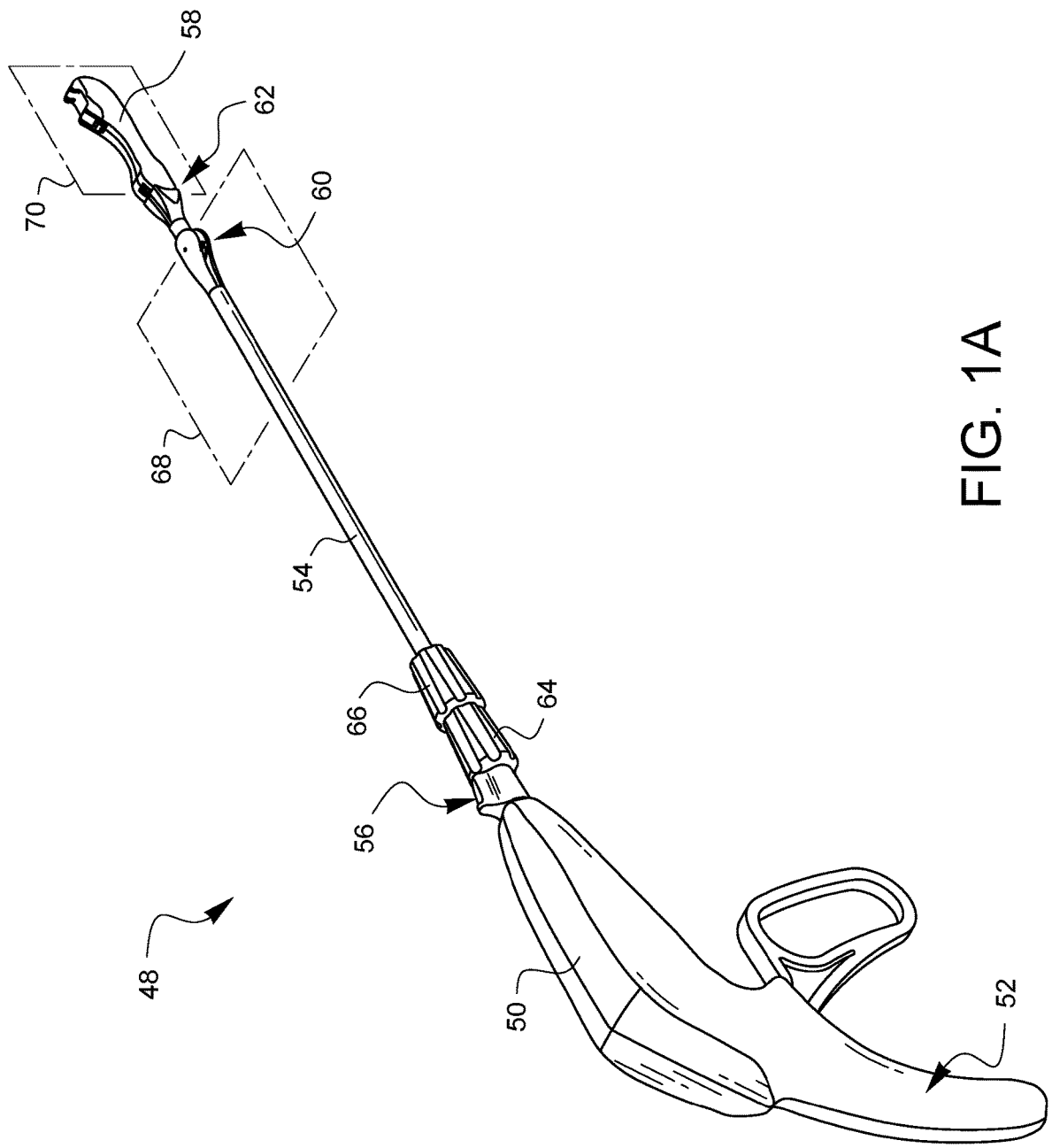
FIG. 1A is a perspective view of one embodiment of a minimally invasive surgical suturing device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A is a perspective view of one embodiment of a minimally invasive surgical suturing device 48. The device 48 has a housing 50 which extends down to form a handle 52. The device 48 also has a shaft 54 which is coupled to the housing 50 by a rotational adapter which is not completely visible in this view. An indicator fin 56 of the rotational adapter can be seen in this view, however.

The device 48 has a distal tip 58 which is pivotably coupled to the shaft 54 by first and second articulation joints 60, 62. The first articulation joint 60 is operationally coupled to a first articulation knob 64 such that rotation of the first articulation knob 64 causes the first articulation joint 60 to articulate the distal tip 58 in a first plane 68. The second articulation joint 62 is operationally coupled to a second articulation knob 66 such that rotation of the second articulation knob 66 causes the second articulation joint to articulate the distal tip 58 in a second plane 70. In this example, the first plane 68 is substantially perpendicular to the second plane 70. In other embodiments having two articulation joints, the two articulation planes may not be substantially parallel. Other embodiments may have more or fewer, including none, articulation joints. The articulation joints in other embodiments may be capable of movement in more than one plane.

Figure 1B:
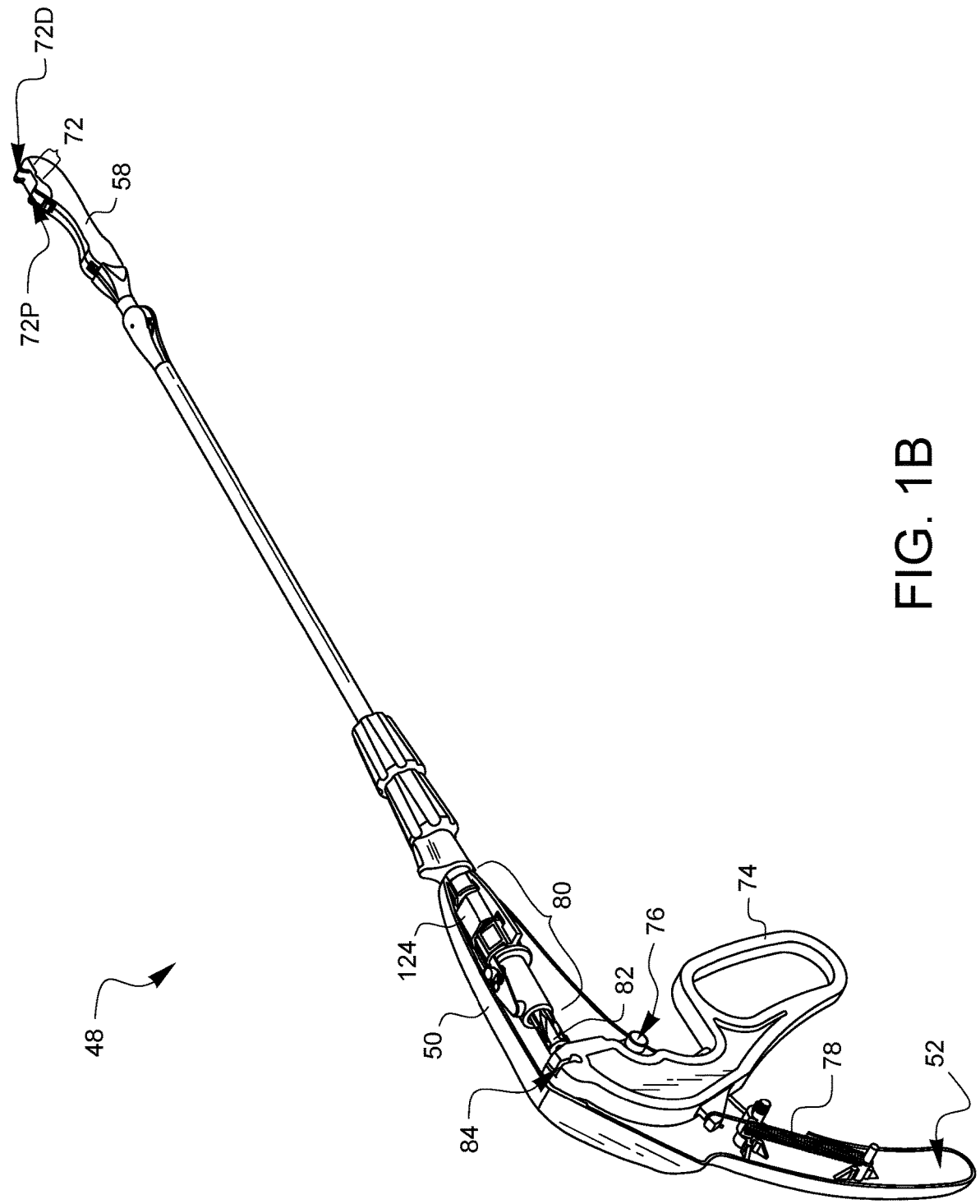
FIG. 1B is a partially exposed view of the minimally invasive surgical suturing device of FIG. 1A.

FIG. 1B is a partially exposed view of the device 48 from FIG. 1A. In particular, part of the housing 50 has been removed so that the components inside may be more clearly seen. The distal tip 58 defines a tissue gap 72. As will be explained in more detail later in this specification, the device 48 may be positioned so that tissue is in the tissue gap 72. Curved needle arms (not visible in this view) are configured to be movable through the tissue gap 72 from the distal end of the gap 72D to the proximal end of the gap 72P. The needle arms (not visible in this view) are coupled to an actuation lever 74 which is pivotable around pivot point 76. A biasing element, such as spring 78 is coupled between the actuation lever 74 and the inside of the handle 52 in order to keep the lever 74 biased away from the handle 52 as illustrated in the retracted position of FIG. 1B. In this retracted position, the needle arms (not visible in this view) remain retracted in the distal tip 58.

The needles are coupled to the lever 74 by a needle control wire (not visible in this view) which runs through the second and first articulation joints 62, 60, the shaft 54, and a rotation adapter 80. Embodiments of rotation adapters 80 are known to those skilled in the art, for example, see U.S. Patent Application Publication No. 2016/0354080, the entirety of which is hereby incorporated by reference. The needle control wire (not visible in this view) also passes through, but is coupled to a twisting barrel 82. The proximal end of the needle control wire (not visible in this view) has a ball which is coupled to a ball receiver 84 on the actuator lever 74. Thus, the needle control wire (not visible in this view) is free to be rotated on its longitudinal axis while still being capable of movement substantially along that longitudinal axis when the actuation lever 74 is squeezed towards the handle 52.

Figure 2B:
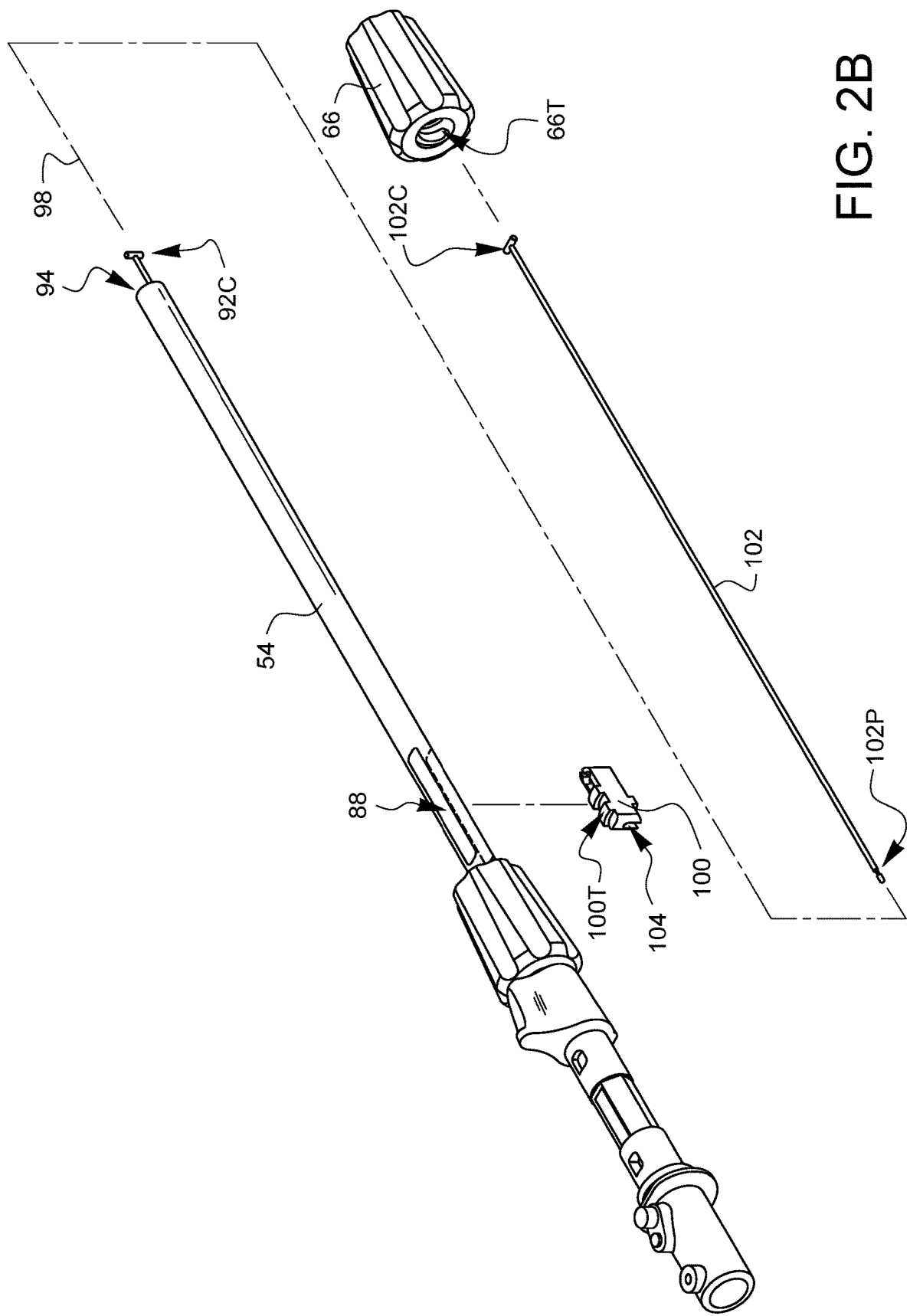

FIGS. 2A-2F are exploded views illustrating assembly of the minimally invasive surgical suturing device 48 of FIGS. 1A and 1B. Referring to FIG. 2A, the shaft 54 is a hollow tube. As currently illustrated in FIG. 2A, the proximal end 54P of the shaft is attached to the rotation adapter. These two parts 54, 80 are not shown exploded, but the proximal end of the shaft 54P inside of the rotation adapter 80 has textured features around which the rotation adapter 80 is molded. The shaft 54 has first and second slots 86, 88 formed near the proximal end of the shaft 54P. A first articulation rack 90 is placed in the first slot 86 and a proximal end 92P of a first articulation control wire 92 is placed into a distal opening 94 in the shaft 54. The proximal end 92P of the first articulation control wire 92 is configured to mate with a corresponding feature 96 on the first articulation rack. The first articulation rack 90 is shorter than the first slot 86, so it is able to be moved back and forth within the first slot 86 in a direction that is substantially parallel to the longitudinal axis 98 of the shaft 54.

The first articulation knob 64 has threads 64T which are pitched to engage gear threads 90T on the first articulation rack 90. The first articulation knob 64 is passed over the shaft 54 and threaded onto the first articulation rack 90. A connector 92C on the distal end of the first articulation control wire 92 extends out of the shaft 54 and can be moved towards the distal opening of the shaft 54 or away from the distal opening of the shaft 54 to the extent that twisting the first articulation knob 64 is able to move the first articulation rack 90 within the first slot 86.

As shown in FIG. 2B, a second articulation rack 100 is placed in the second slot 88 and a proximal end 102P of a second articulation control wire 102 is placed into the distal opening 94 in the shaft 54. The proximal end 102P of the second articulation control wire 102 is configured to mate with a corresponding feature 104 on the second articulation rack 100. The second articulation rack 100 is shorter than the second slot 88, so it is able to be moved back and forth within the second slot 88 in a direction that is substantially parallel to the longitudinal axis 98 of the shaft 54.

The second articulation knob 66 has threads 66T which are pitched to engage gear threads 100T on the second articulation rack 100. The second articulation knob 66 is passed over the shaft 54 and threaded onto the second articulation rack 100. A connector 102C on the distal end of the second articulation control wire 102 extends out of the shaft 54, farther than the first connector 92C, and can be moved towards the distal opening 94 of the shaft 54 or away from the distal opening 94 of the shaft 54 to the extent that twisting the second articulation knob 66 is able to move the second articulation rack 100 within the second slot 88.

Figure 2C:
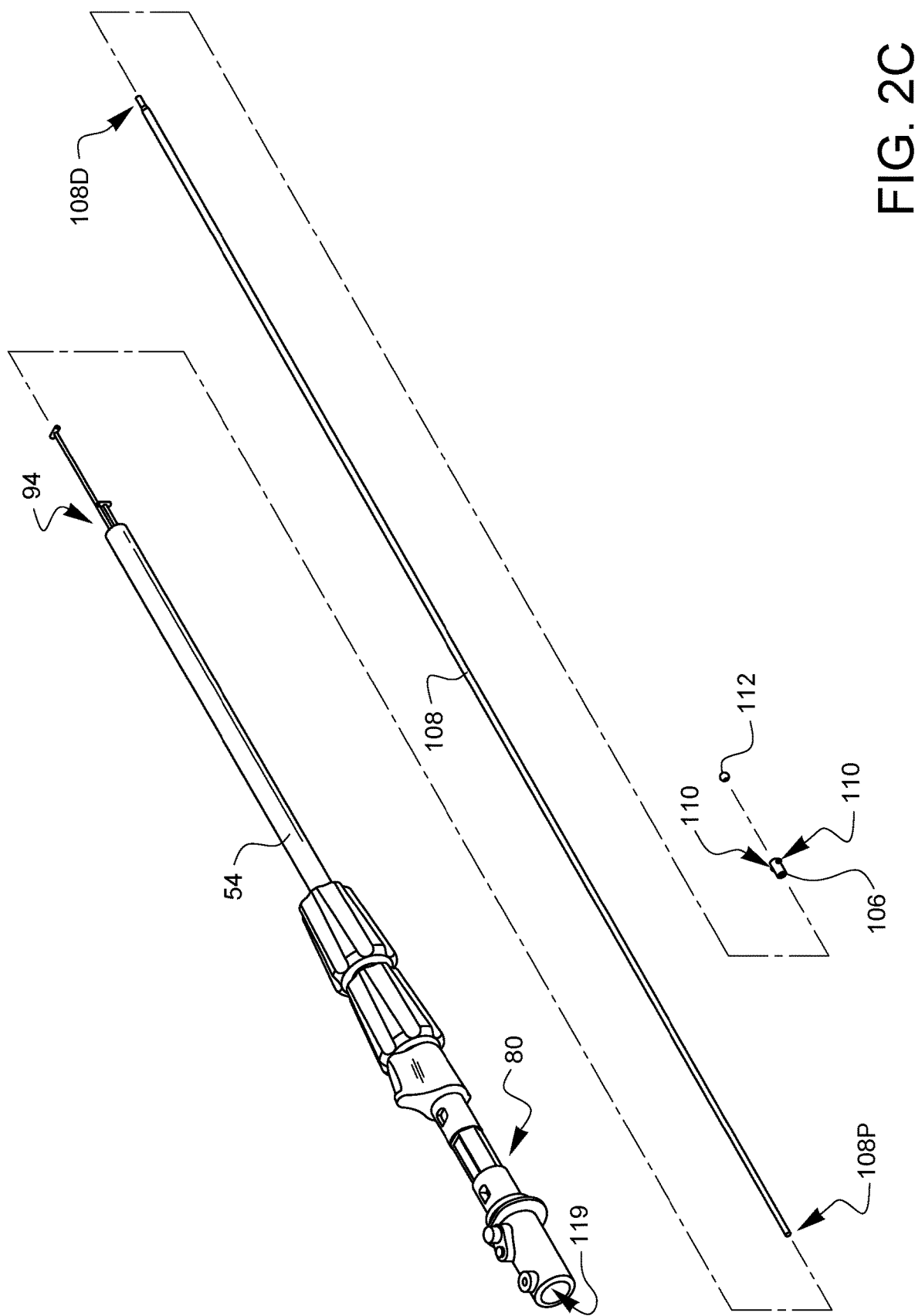

As shown in FIG. 2C, a collar 106 is placed over the distal end 108D of a needle control wire 108. In this embodiment, the collar 106 has two cams 110. As will be discussed in more detail later in this specification, the cams 110 will be moved into and out of phase with a follower surface of a ferrule latch (not shown in this view). The exact position of the collar 106 on the a proximal end 108P of the needle control wire 108 can be determined by those skilled in the art to effect the cam behavior discussed later in this specification. A distal ball end 112 is attached to the distal end 108D of the needle control wire 108. The proximal end 108P of the needle control wire is inserted into the distal opening 94 of the shaft 54 and passed all the way through the shaft 54, through the rotational adapter 80, and out the actuator input 114 of the rotational adapter.

Figure 2D:
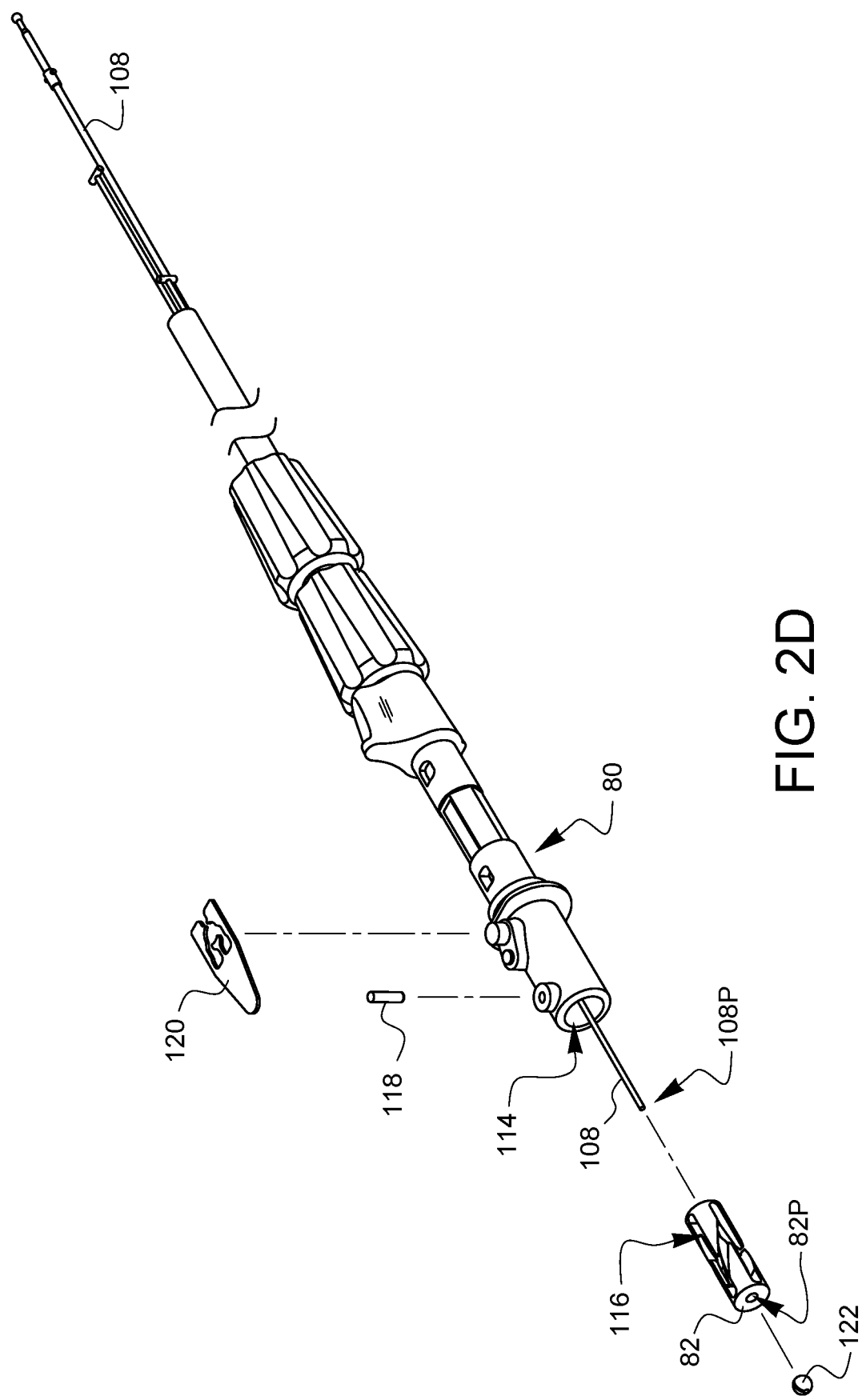

As illustrated in FIG. 2D, the proximal end 108P of the needle control wire 108 is passed through the twisting barrel 82 so that it protrudes out the proximal end 82P of the barrel 82. The barrel 82 is then fixed to the needle control wire 108 such that it enters the actuator input 114 of the rotational adapter 80. The barrel 82 has cam paths 116 which are engaged by a cam pin 118 biased against the barrel 82 by a cam spring 120 that is coupled to the rotation adapter 80. A proximal ball end 122 is attached to the proximal end 108P of the needle control wire 108. The proximal ball end 122 is coupled to the ball receiver 84 of actuation lever 74 as shown in FIG. 1B. The housing 50 and one or more rotation adapter receivers 124 stabilize the rotation adapter 80.

Figure 2E:
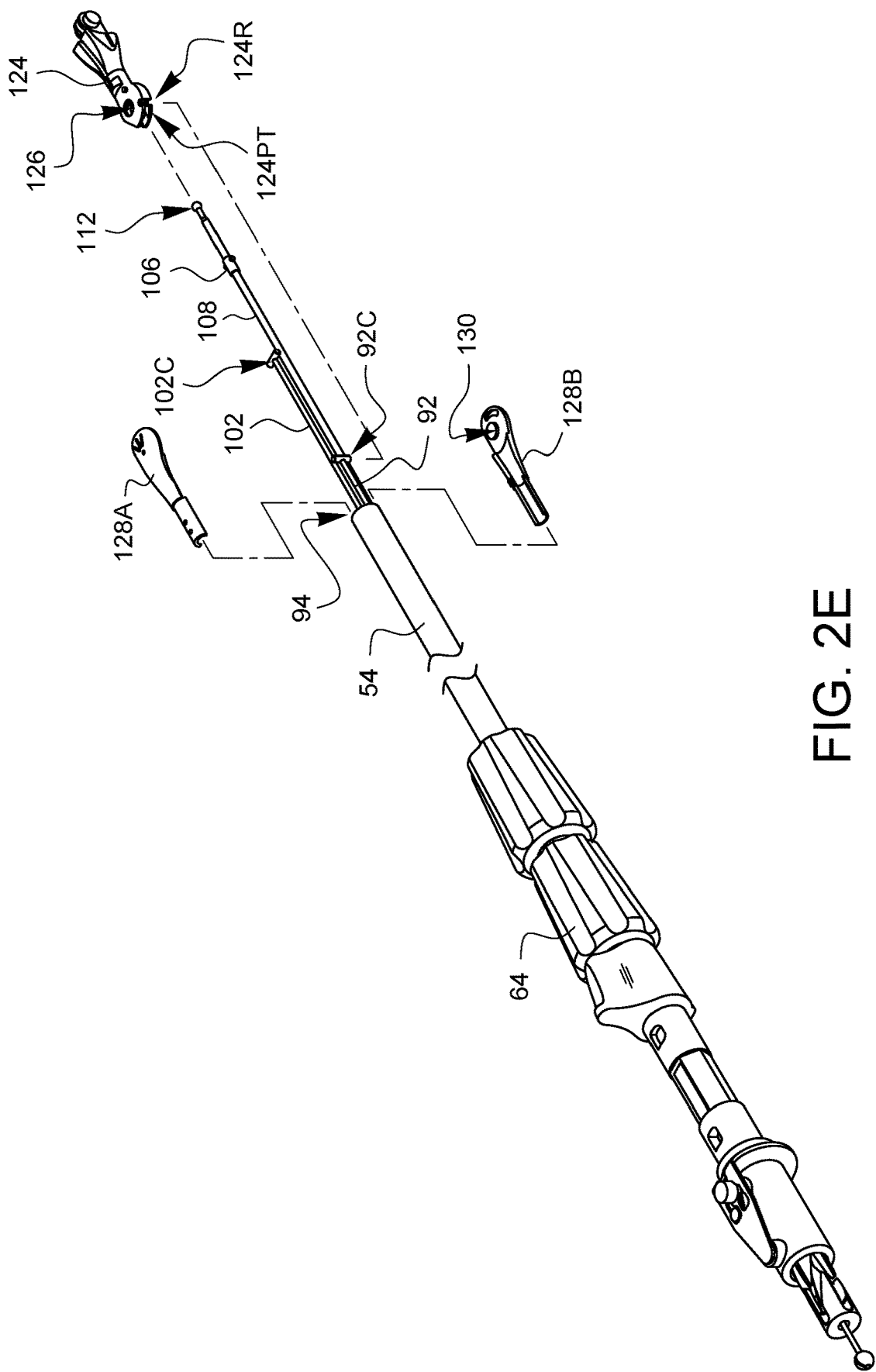

For simplicity, FIG. 2E does not show the housing 50, actuation lever 74, spring 78, or the rotation adapter receiver 124 so that the assembly of the distal end of the device may be seen more clearly. Recall that the first articulation control wire 92 and the connector 92C at its distal end protrude from the distal opening 94 of the shaft 54. Similarly, the second articulation control wire 102 and the connector 102C at its distal end protrude farther from the distal opening 94 of the shaft 54. Furthermore, the needle control wire 108 and the collar 106 and distal ball end 112 protrude even father from the distal opening 94 of the shaft 54. As illustrated in FIG. 2E, a first pivotable arm 124 has a first connector receiver 124R and a pass-through channel 124PT. The needle control wire 108 and the second articulation control wire 102 are fed through the pass-through channel 124PT in the arm 124, and then the arm 124 is positioned so the first connector receiver 124R receives the connector 92C from the first articulation control wire 92. The first pivotable arm 124 also has an axle receiving opening 126. Two fixed arm halves 128A, 128B are inserted into the distal end 94 of the shaft 54 while being brought together around the first pivotable arm 124. The fixed arm halves 128A, 128B each have an axle 130 (only one of which is visible in FIG. 2E). The axles 130 are aligned with the axle receiving opening 126 on the first pivotable arm 124. Together, the first pivotable arm 124 and the fixed arm halves 128A, 128B which support and provide an axle for the first pivotable arm 124 make up the first articulation joint 60 first discussed in FIG. 1A. Movement of the first articulation control wire 92 caused by rotation of the first articulation control knob 64 will cause the first pivotable arm 124 to pivot or articulate with respect to the fixed arm halves 128A, 128B.

Figure 2F:
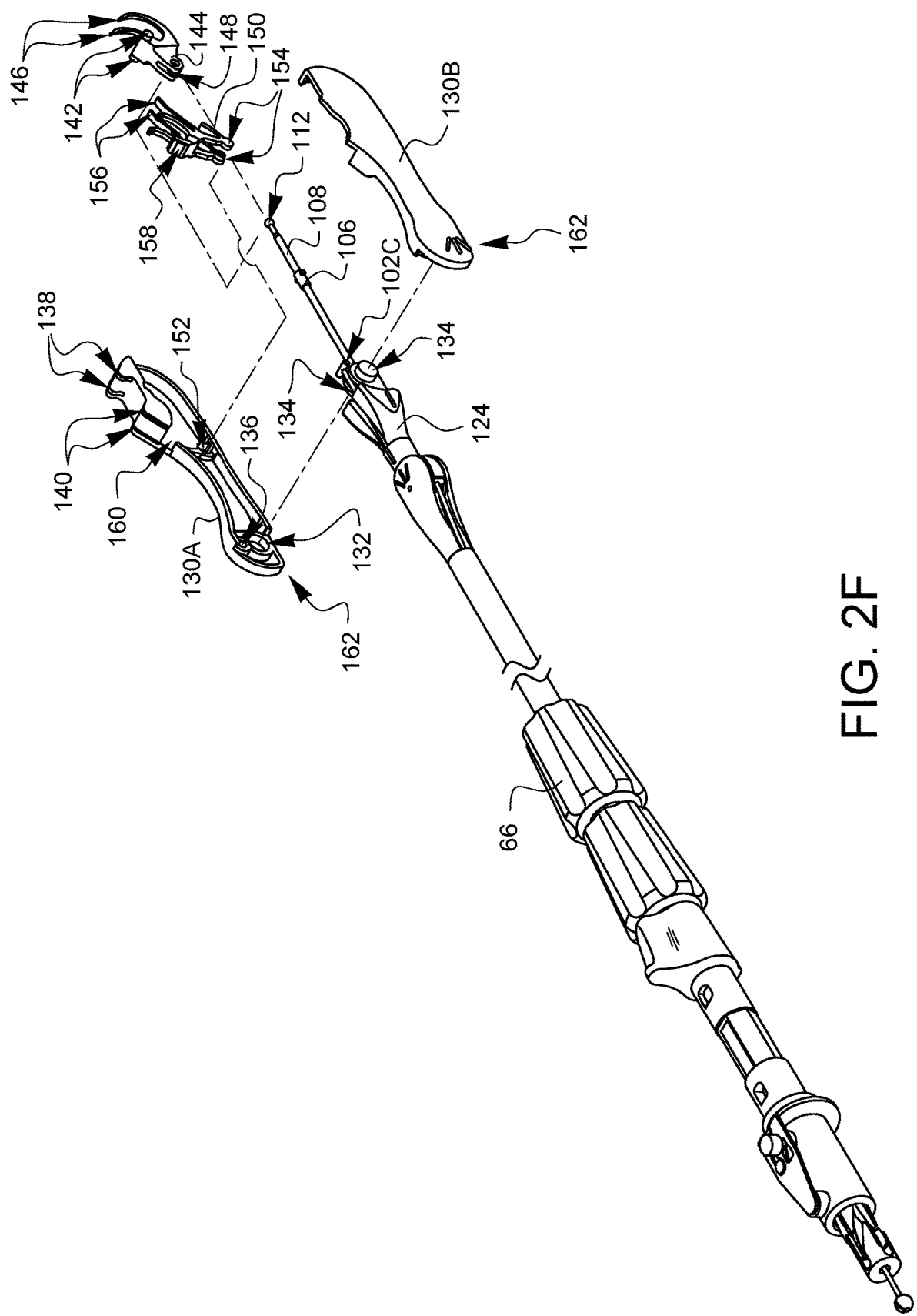

As illustrated in FIG. 2F, the distal tip has two casing halves 130A, 130B. Each casing half 130A, 130B has an axle receiver 132 (only one of which is visible in FIG. 2F). The first pivotable arm 124 has a corresponding pair of axles 134. Each casing half 130A, 130B also has a connector receiver 136 (only one of which is visible in FIG. 2F). The connector receivers 136 are sized to receive part of the connector 102C. The casing half 130A defines needle arm exit holes 138 and ferrule holders 140. Although not visible in this view, the casing halves 130A, 130B also define receivers for the axles 142 of the needle 144. When the axles 142 are held by the axle receivers (not visible in this view), the needle 144 may be pivoted so that the needle arms 146 will protrude from the needle arm exit holes 138. The needle 144 also has a receiver 148 for receiving the distal ball end 112 and allowing clearance for the needle control wire 108.

A latch spring 150 is also involved. The casing halves 130A, 130B each define a spring pivot receiver 152 (only one if which is visible in FIG. 2F). The spring pivot receivers 152 are sized to receive corresponding pivot points 154 from the latch spring 150. Further details of the latch spring 150 will be discussed later in this specification, but it should be noted here that the latch spring has a channel which allows the needle control wire 108 to pass freely therethrough.

To complete the assembly of FIG. 2F, the casing halves 130A, 130B must be brought together so that 1) the axles 134 are aligned with the corresponding axle receivers 132, 2) the connector 102C is aligned with the corresponding connector receivers 136, 3) the distal ball end 112 is coupled to the receiver 148 on the needle 144, 4) the needle axles 142 are aligned with the axle receivers (not visible in this view) of the casing halves 130A, 130B, and 5) the pivot points 154 of the latch spring 150 are aligned with the spring pivot receivers 152 while 6) biasing elements 156 of the latch spring 150 ride up on portions of the needle 144, 7) a manual latch defeat 158 of the latch spring 150 is aligned within a defeat opening 160 of the casing half 130A, and 8) the needle control wire passes through the pivot points 154 of the latch spring 150 as the casing halves 130A, 130B are coupled and affixed to each other. Together, the proximal end of the device tip 162 (made from the casing halves 130A, 130B) and the distal end of the first pivotable arm 124 make up the second articulation joint 62 discussed in FIG. 1A. Movement of the second articulation control wire 102 caused by rotation of the second articulation control knob 66 will cause the distal tip casing 130A, 130B to pivot or articulate with respect to the arm 124.

Figure 3A:
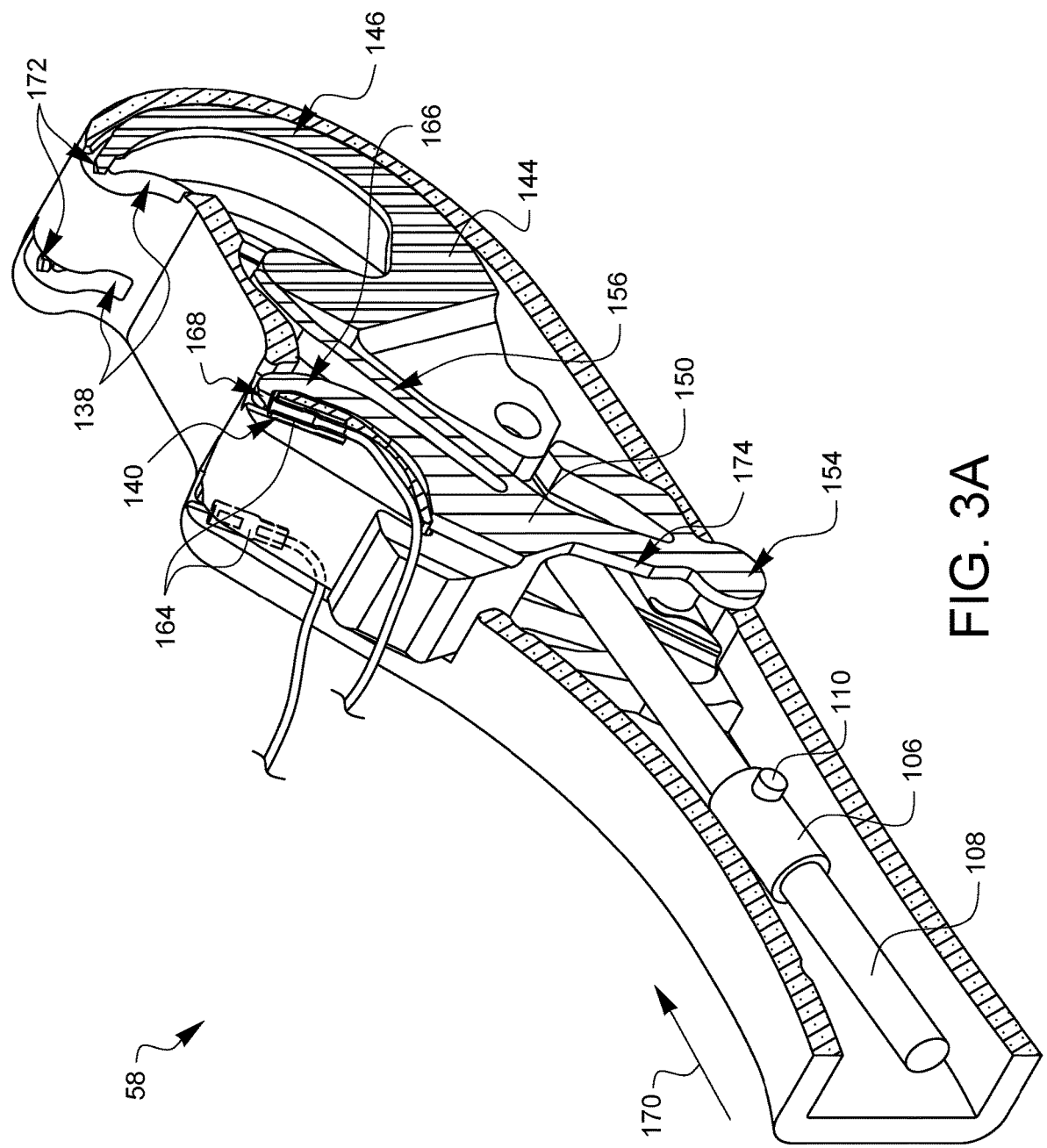
FIGS. 3A and 3B are partial cross-sectional perspective views of the distal tip of the device of FIG. 1A.
Figure 3B:
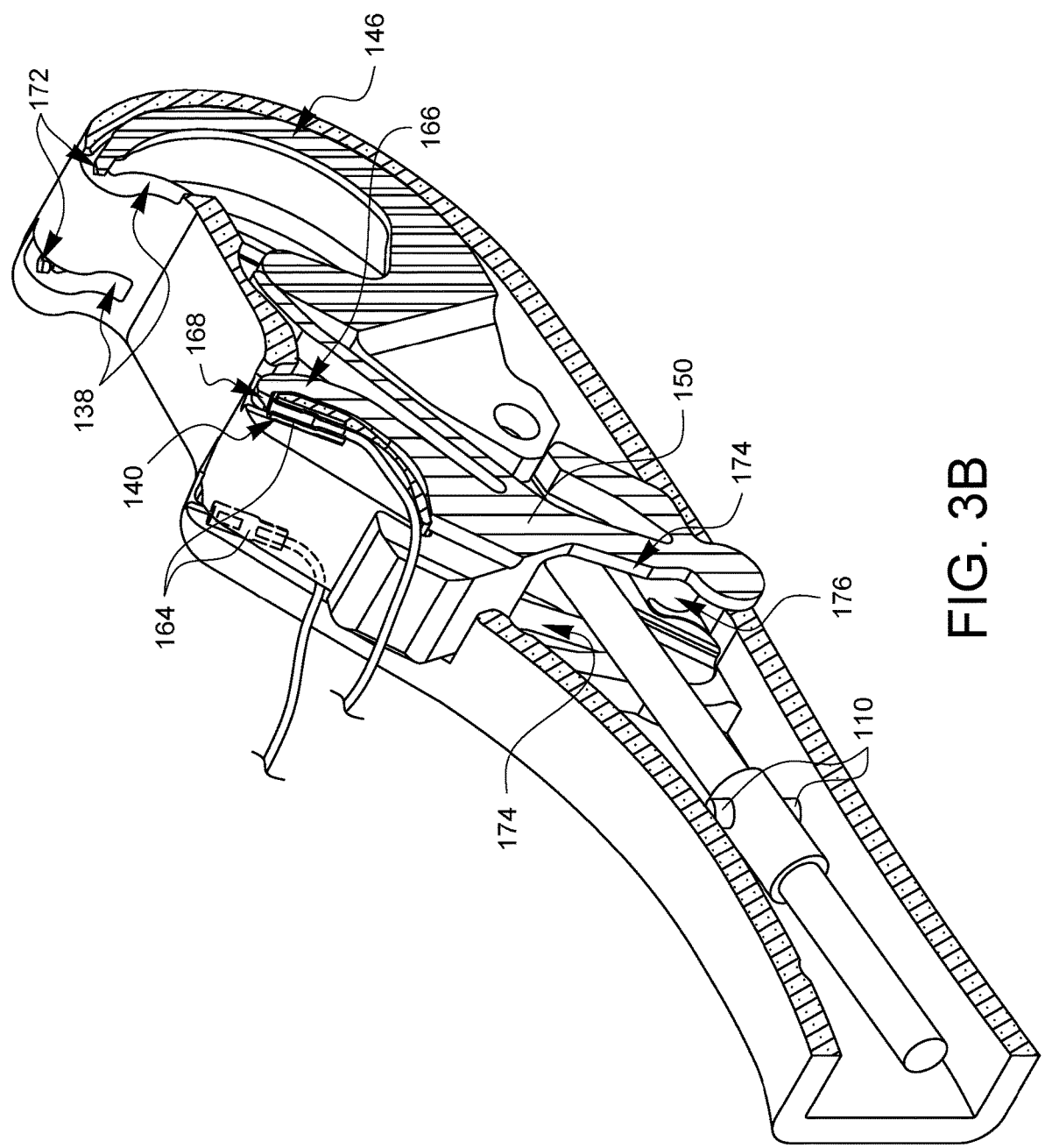

FIGS. 3A and 3B are partial cross-sectional perspective views of the distal tip 58 which offer more clarity on the orientation of the collar 106 and the cams 110 with respect to the latch spring 150. For the sake of explanation, a ferrule 164 has been loaded into one of the ferrule holders 140. The latch spring 150 has two latch arms 166, one corresponding to each ferrule holder 140. The latch arms 166 are coupled to the pivot point 154, but are biased towards the ferrule holders 140 by biasing elements 156. Without any other forces interacting with the latch arms 166, the biasing elements 156 cause the latch arms 166 to pivot about the pivot points 154 towards the ferrule holders 140 so that the latch 168 at the end of each latch arm 166 holds its corresponding ferrule 164 in the ferrule holder 140.

The needle control wire 108 will move distally 170 when the actuation lever 74 is squeezed. As will be discussed later in this specification, this will cause the arms 146 of needle 144 to rotate out of the device tip 58 from the needle arm exit holes 138, moving proximally on a curved or arcuate path towards the ferrules 164 held in the ferrule holders 140. However, while the latch 168 is holding the ferrule 164, the needle tips 172 will not be able to remove the ferrules 164 from the ferrule holders 140. Fortunately, with this design embodiment, and its equivalents, the cams 110 are oriented such that they will contact follower regions 174 on the latch spring 150 as the needle control wire 108 moves distally. This contact of the cams 110 with the follower regions of the latch spring 150 overcomes the bias from the biasing elements 156 and pushes the latch arms 166 away from the ferrule holders 140 such that the latches 168 are no longer preventing the ferrules 140 from being removed by the needle tips 172 as will be discussed later on with regard to FIGS. 4A, 5A, 6A, 7A, 8A, 9A, and 10A.

The design of the rotating barrel 82 which engages with the cam pin 118 is such that as the actuator lever is released the cam paths 116 on the barrel 82 cause the needle control wire 108 to rotate ninety degrees while the needle control wire 108 moves in a proximal direction to retract the needle arms 146. This will effectively align the cams 110 at ninety degrees from the FIG. 3A position, as shown in FIG. 3B. When the cams are aligned as shown in FIG. 3B, a subsequent squeeze of the actuation lever 74 will again cause the needle control wire to move in a distal direction, causing the arms 146 of needle 144 to rotate out of the device tip 58 from the needle arm exit holes 138, moving proximally on a curved or arcuate path towards the ferrules 164 held in the ferrule holders 140. This time, however, with the cams 110 ninety degrees out of phase, the cams 110 will not contact the follower regions 174 on the latch spring 150. Instead, the cams 110 will simply pass through the clearance gap 176 defined by the latch spring 150 between the follower regions 174. This clearance gap 176 cannot be seen in the following side views, so FIG. 3B can be consulted as desired to visualize the clearance gap 176. When the cams 110 pass through the clearance gap 176 without contacting the follower regions 174, then the latches 168 remain engaged with the ferrule holders 140.

FIGS. 4A, 5A, 6A, 7A, 8A, 9A, and 10A are partial cross-sectional side views illustrating a suturing sequence using the minimally invasive suturing device 48 discussed herein. Each of FIGS. 4A, 5A, 6A, 7A, 8A, 9A, and 10A has a corresponding enlarged view, FIGS. 4B, 5B, 6B, 7B, 8B, 9B, and 10B, respectively. The enlarged views show the distal tip in more detail. For convenience, only FIGS. 4A, 5A, 6A, 7A, 8A, 9A, and 10A will be discussed, but it should be understood that the enlarged views of FIGS. 4B, 5B, 6B, 7B, 8B, 9B, and 10B may also be consulted for more detail. Also, since 4A, 5A, 6A, 7A, 8A, 9A, and 10A are from a side view, only one needle arm, ferrule holder, ferrule, needle tip, latch, etc may be seen in these views. For convenience, therefore, only the one visible version of each component will be discussed, however, it is understood that there is a corresponding other component behind the visible component.

In FIG. 4A, at the start of the sequence, a ferrule 164 has been loaded into the ferrule holder 140. The latch 168 is positioned over the ferrule holder 140. The actuation lever 74 is in the unsqueezed position and the needle arm 146 is retracted inside of the distal tip 58. The cam 110 is oriented in an unlatching phase, whereby the cam 110 will contact the follower region 174 of the latch spring 150 when the lever 74 is eventually squeezed. The tissue gap 72 of the device has been placed around tissue 178 through which it is desired to place the suture 180 which is coupled to the ferrule 164.

Figures 5A, 5B:
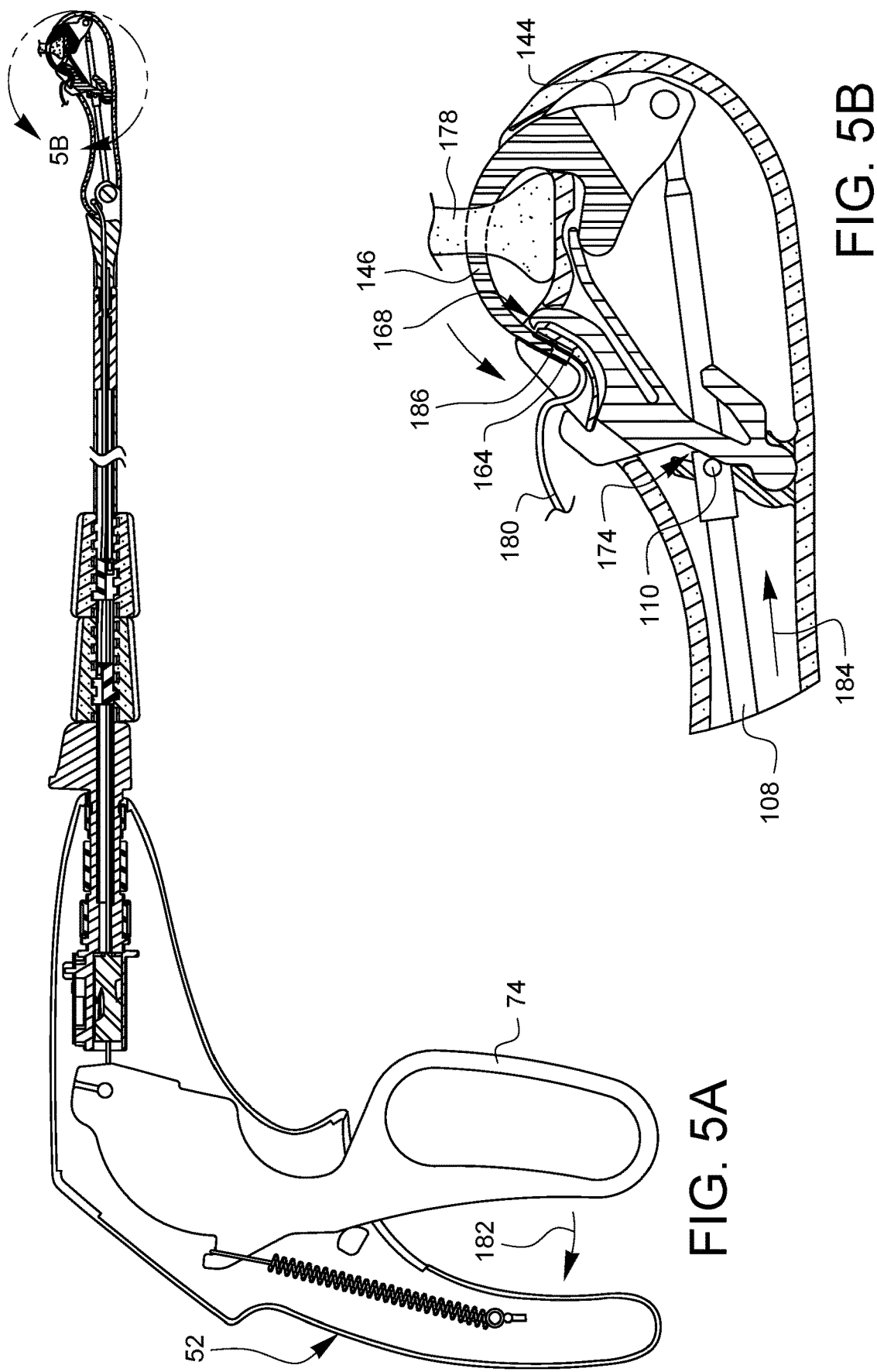

As shown in FIG. 5A, the lever 74 is squeezed 182 towards the handle 52. The needle control wire 108 moves distally 184, causing the cam 110 to contact the follower region 174 and pivoting the latch 168 away from the ferrule holder 140. The distal movement 184 of the needle control wire 108 also rotates the needle 144 so the needle arm 146 penetrates the tissue 178 and the needle tip 186 engages the ferrule 164.

As shown in FIG. 6A, the lever 74 is starting to be released 188. The needle control wire 108 starts to move proximally 190, but the cam 110 is still in contact with the follower region 174 of the latch spring 150. This keeps the latch 168 clear of the ferrule holder 140 while the needle arm 146 rotates 192 distally back along its curved path, allowing the ferrule 164 to be removed from the ferrule holder 140 by the needle tip 186.

As the lever 74 is fully released, as shown in FIG. 7A, the cam 110 disengages the follower region 174 and the needle control wire 108 is rotated ninety degrees as discussed above. The biasing element 156 of the latch spring 150 has again pushed the latch 168 over the ferrule holder 140. The needle arm 146 is fully retracted, and the needle tip 186 has pulled the ferrule 164 and its suture 180 back through the tissue 178.

Figure 9A:
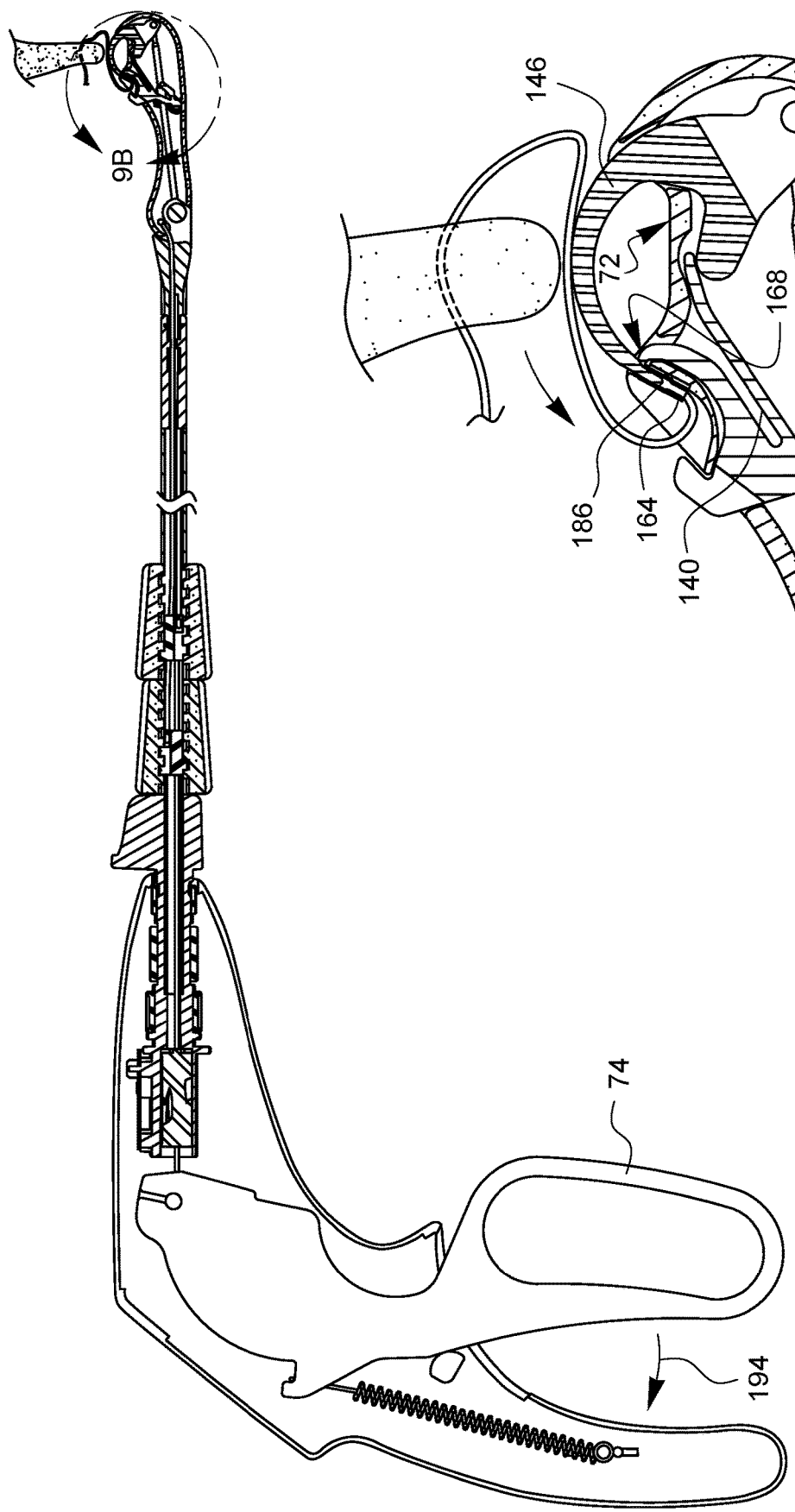
Figure 9B:
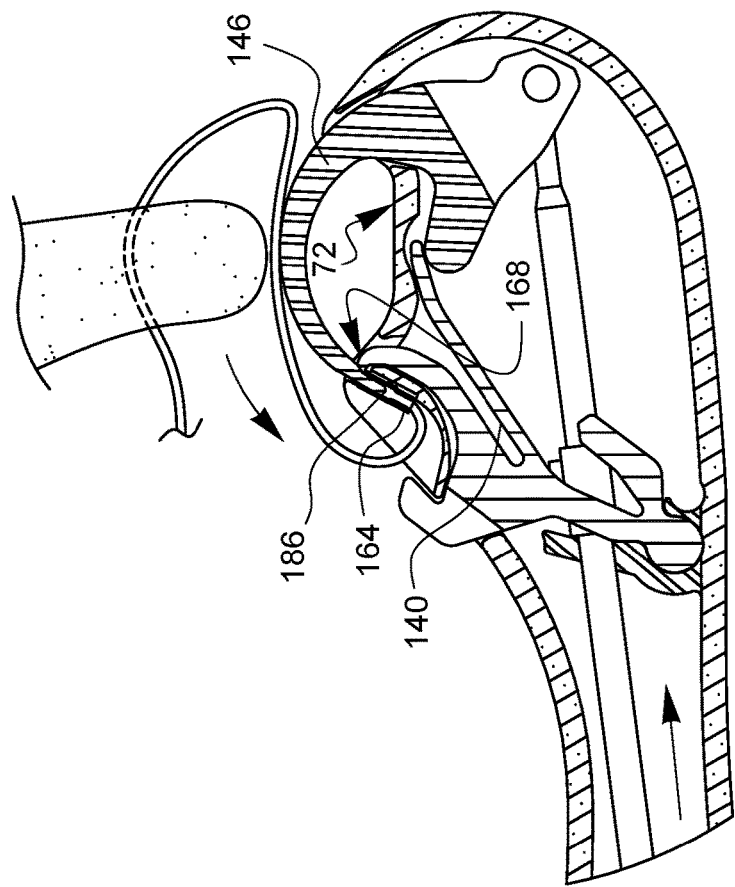

As shown in FIG. 8A, the tissue gap 72 is removed from the tissue 178. It may be desirable to reset the suturing device so that a subsequent stitch may be placed. While there is no tissue 178 in the tissue gap 72, as shown in FIG. 9A, the lever 74 may be squeezed 194 again. The needle tip 186 with its engaged ferrule 164 moves across the tissue gap 72, returning the ferrule 164 to the ferrule holder 140. Since the cam 110 is oriented to pass through the clearance gap 176 (not visible in this view), the latch 168 rides over the ferrule 164 and then comes to rest on the needle arm 146 just above the ferrule 164. When the lever 74 is released 198 as shown in FIG. 10A, the latch 168 pulls the ferrule 164 off of the needle tip 186 as the needle arm 146 retracts. The needle control wire 108 rotates ninety degrees as it moves proximally 198, as discussed above. This resets the cam 110 to the position of FIG. 4A. The ferrule 164 is also reset in the ferrule holder 140, and the device is ready to place a second stitch.

By being able to reset the ferrule by squeezing the lever after taking a first stitch, the device can be called a "running-stitch" device, capable of making multiple suture stitches in vivo, through a minimally invasive access opening, without the need to remove the device and manually reset between stitches. This may be especially helpful in the replacement of chordae tendinae of a mitral valve leaflet, as a first stitch may be placed in a leaflet, the device reset, and then a second stitch placed in a papillary muscle. The second stitch may be secured after adjusting the length of the suture between the leaflet and the papillary muscle to a desired distance to reduce or eliminate leaflet prolapse.

Figure 11A:
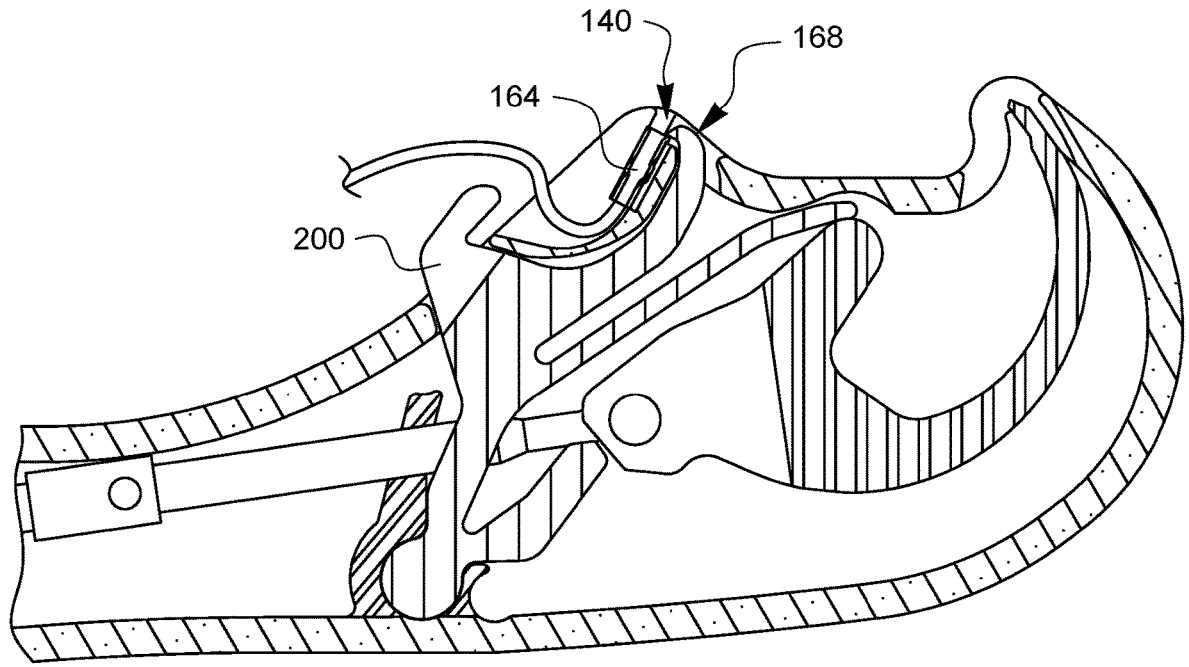
FIGS. 11A and 11B are partial side cross-sectional views of an embodiment of a distal tip of a minimally invasive surgical suturing device which has one embodiment of a manual latch defeat for allowing a ferrule to be taken out of a ferrule holder so the device can be loaded with more suture having ferrules and used again, if so desired.
Figure 11B:
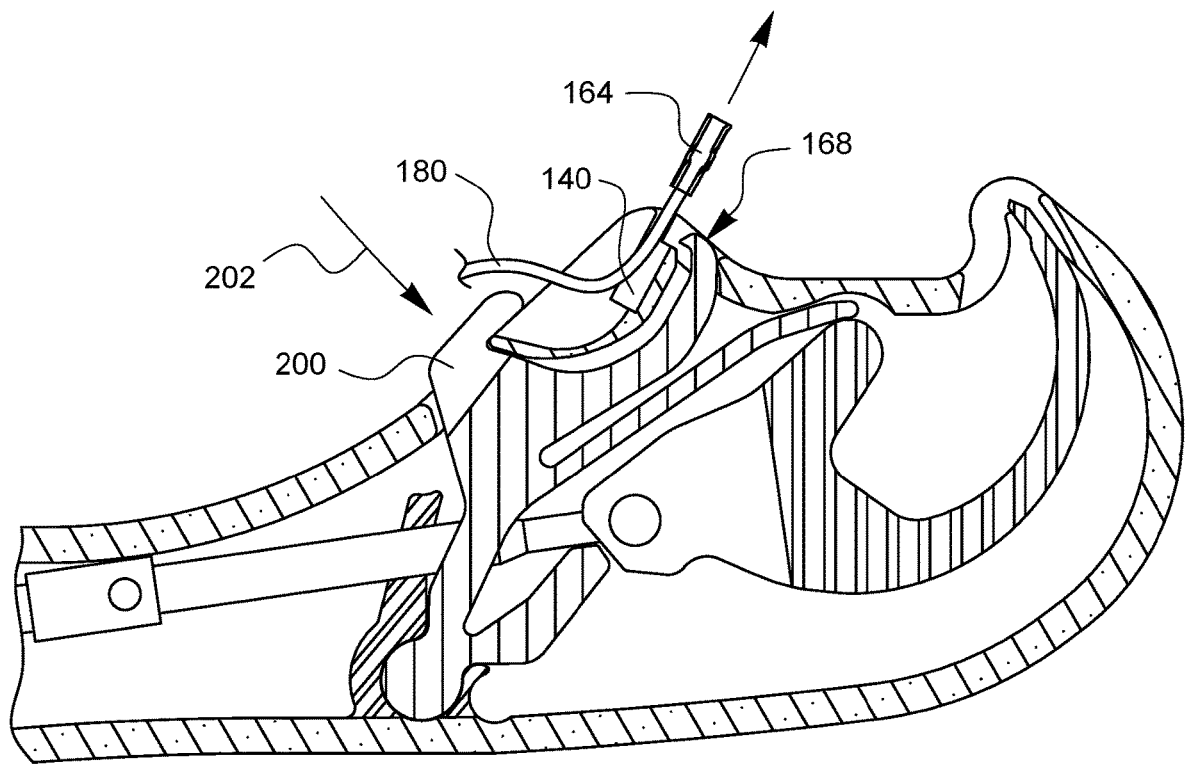

When the desired stitches have been placed, it is still necessary to remove the ferrules from the suturing device. While the ferrules could simply be cut from the suture, this may make the suturing device unusable with other sutures because the ferrules will either be attached to the needle tips or kept housed in the ferrule holders. Accordingly, a manual latch defeat 158 may be incorporated into the latch spring 150. To remove the suture 180 and ferrules 164 from the device, the ferrules 164 should be returned to the ferrule holders 140 as shown above. This is the situation shown in FIG. 11A. As can be seen in FIG. 11A, the latch 168 is positioned to retain the ferrule 164 in the ferrule holder 140. As shown in FIG. 11B, the manual latch defeat 200 may be pressed 202 to push the latch 168 away from the ferrule holder 140. This allows the ferrule 164 to be taken out of the ferrule holder 140, thereby keeping the device in good order to be loaded with more suture having ferrules and used again if so desired.

Various advantages of a suturing device for minimally invasive surgery have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As just some examples, a similar latch spring could be used with a curved needle suturing device whose needles extend across the tissue gap in an opposite direction from the device discussed herein. Also, the latch spring could be configured to work with multiple more or fewer needles. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. A suturing device for minimally invasive surgery, comprising:
  at least one ferrule holder;
  a latch spring comprising a follower region and at least one latch biased to cover the at least one ferrule holder;
  a needle comprising one or more curved needle arms;
  a needle control wire coupled to the needle; and
  a cam coupled to a distal end of the needle control wire for selective contact with the follower region on the latch spring.

2. The suturing device of claim 1, wherein the at least one latch is biased to partially cover the at least one ferrule holder.

3. The suturing device of claim 1, wherein the needle control wire passes through an opening in the latch spring.

4. The suturing device of claim 1, wherein:
the at least one ferrule holder comprises two ferrule holders;
the at least one latch is biased to cover the two ferrule holders; and
the one or more curved needle arms comprise two curved needle arms.

5. The suturing device of claim 1, further comprising:
a handle and at least one needle arm exit hole.

6. The suturing device of claim 5, wherein the at least one ferrule holder is proximal to the needle arm exit hole.

7. The suturing device of claim 1, wherein the cam comprises a collar coupled to the needle control wire.

8. The suturing device of claim 1, wherein the latch spring further comprises a biasing element.

9. The suturing device of claim 1, wherein the latch spring further comprises a manual latch defeat.

10. The suturing device of claim 1, further comprising a barrel having a curved cam path coupled to a proximal end of the needle control wire.

11. The suturing device of claim 10, wherein the barrel is movable between a latching phase and an unlatching phase such that:
a) the cam coupled to the distal end of the needle control wire contacts the follower region of the latch spring when the barrel is in the latching phase; and
b) the cam coupled to the distal end of the needle control wire passes through a clearance gap defined by the latch spring when the barrel is in the unlatching phase.

12. The suturing device of claim 1, wherein the needle control wire coupled to the needle moves the one or more curved needle arms on an arcuate path through a tissue gap.

* * * * *